United States Patent [19]

Baba et al.

[11] 4,216,337

[45] Aug. 5, 1980

[54] PROCESS FOR PREPARING ESTERS

[75] Inventors: Makoto Baba, Kurashiki; Teruyuki Ninomiya; Chieko Ono, both of Okayama, all of Japan

[73] Assignee: Mitsubishi Gas Chemical Co., Inc., Japan

[21] Appl. No.: 923,406

[22] Filed: Jul. 10, 1978

Related U.S. Application Data

[63] Continuation-in-part of Ser. No. 756,605, Jan. 4, 1977, abandoned.

[30] Foreign Application Priority Data

Jan. 13, 1976 [JP] Japan ................................. 51-3033
Jan. 30, 1976 [JP] Japan ................................. 51-8987

[51] Int. Cl.$^2$ ............................................. C07C 67/48
[52] U.S. Cl. ................................... 560/78; 260/347.4; 560/19; 560/20; 560/50; 560/79; 560/127; 560/180; 560/182; 560/191
[58] Field of Search .................. 560/78, 79, 191, 19, 560/20, 50, 180, 182, 127; 260/347.4

[56] References Cited

U.S. PATENT DOCUMENTS

| | | | |
|---|---|---|---|
| 2,776,984 | 1/1957 | Mention et al. | 560/191 |
| 2,862,958 | 12/1958 | Goreau | 560/78 |
| 2,912,457 | 11/1959 | Blaser et al. | 560/78 |
| 2,938,837 | 5/1960 | Meyer et al. | 560/78 |
| 3,293,282 | 12/1966 | Farrar et al. | 560/78 |
| 3,818,071 | 6/1974 | Chilton | 560/78 |

FOREIGN PATENT DOCUMENTS

| | | | |
|---|---|---|---|
| 2042402 | 3/1972 | Fed. Rep. of Germany | 560/78 |
| 329167 | 3/1972 | U.S.S.R. | 560/78 |

*Primary Examiner*—Jane S. Myers
*Attorney, Agent, or Firm*—Wenderoth, Lind & Ponack

[57] ABSTRACT

A process for preparing esters which comprises reacting a polycarboxylic acid with an alcohol, removing the unreacted alcohol from the resultant esterification reaction mixture, heating the crude ester at a temperature of 160° to 340° C., contacting the heat-treated crude ester with an adsorbent, and recovering the ester of high purity. The ester obtained has superior electrical insulation, transparency and thermal stability.

11 Claims, 4 Drawing Figures

PROCESS FOR PREPARING ESTERS

This application is a continuation-in-part application of U.S. Ser. No. 756,605 filed on Jan. 4, 1977, now abandoned.

This invention relates to a novel process for preparing esters having superior electric insulation, transparency and thermal stability by removing impurities such as acidic substances and water from the esterification reaction mixture obtained.

Esters formed by the reaction of polycarboxylic acids with alcohols are used mainly as plasticizers for thermoplastic synthetic resins, and are required to have superior electric insulation, transparency and thermal stability.

The esterification reaction mixtures obtained by reacting polycarboxylic acids with alcohols contain impurities such as unreacted polycarboxylic acids, unreacted alcohols, half esters of the polycarboxylic acids, low boiling by-products such as olefin, water resulting from the esterification reaction, coloring substances, traces of heavy metal salts and other inorganic substances occurring in the starting substances, and sometimes the catalyst. Of these impurities, acidic substances such as the polycarboxylic acids and their half esters, water, coloring substances, heavy metal salts, and other inorganic substances remain in the final ester products even after purification, and markedly deteriorate their electric insulation, transparency and thermal stability. It is necessary therefore to minimize the amounts of these remaining substances in ester products. For this purpose, the contents of these substances in the esterification reaction mixture must be reduced.

Various methods have been suggested heretofore in order to remove acidic substances such as polycarboxylic acids and their half esters present in the esterification reaction mixtures. For example, some methods have been known to neutralize acidic substances in the esterification reaction mixture followed by washing with water. These neutralizing methods, however, have the defect that a great quantity of water is required, and the coloring substances, heavy metal salts and other inorganic substances present in the esterification reaction mixture remain unremoved and are carried over to the esters finally obtained.

A method was also suggested which involves removing acidic substances, coloring substances, heavy metal salts and other inorganic substances present in the esterification reaction mixture by adsorption using solid adsorbents having the ability to adsorb these substances. According to this method, the ester becomes neutral after adsorption treatment, but when heated further in a purification step or use, it becomes acidic or colored even in the absence of a strongly alkaline neutralizing agent, and the product does not have sufficient electric insulation, transparency and thermal stability.

Known methods for improving the electric insulation and thermal stability of esters produced by ordinary methods include, for example, the method disclosed in Japanese Patent Publication No. 11358/64 which comprises contacting the ester purified by a customary method, with magnesium oxide, and then separating the magnesium oxide thereby to improve the properties of the ester, such as electrical resistance, thermal stability, color and acid number, of the ester, and the method disclosed in Japanese Patent Publication No. 35045/70 which comprises treating dioctyl phthalate or dioctyl adipate with solid calcium hydroxide, which has been pre-treated with water and dried, in a substantially anhydrous condition thereby to greatly improve the volume inherent resistivity of the ester, reduce its acid number, and improve the color and thermal stability of the ester. These methods give rise to some improvement in the electric insulation of the esters. But when such an ester is heated in use, part of it undergoes a saponification reaction, and the final ester still lacks thermal stability to suffer from poor electric insulation and transparency. Furthermore, the process steps become complicated since steps for improving the properties of the esters should be attached to an ordinary ester-purification step.

Accordingly, there has been a strong demand in the art for the development of quite a new method which can eliminate the defects of the above-mentioned methods for preparing esters or improving the properties of esters, and can efficiently afford esters having superior electric insulation, transparency, and thermal stability without substantially yielding industrial wastes.

The present inventors have made extensive investigations to determine why the neutralized ester obtained by removing acidic substances present in the esterification reaction mixture by conventional methods becomes acidified on heating, and causes a deterioration in the electric insulation, transparency and thermal stability of the ester. These investigations led to the discovery that half esters of polycarboxylic acids or alkali metal salts of the half esters are soluble in the final esters, and that these substances cannot be completely removed by neutralization, water washing, adsorption, filtration, sedimentation, extraction, distillation, or combinations of these, but remain in the neutralized ester after treatment. It was further found that the half esters of polycarboxylic acids remaining in the neutralized ester after treatment undergo a double decomposition reaction on heating and afford free polycarboxylic acids in accordance with the following formulae I to IV, for example, and deteriorate the electric insulation of the ester as a final product or thermoplastic synthetic resins plasticized with such an ester, and color thermoplastic synthetic resins.

-continued

Tris(2-ethylhexyl) trimellitate    Trimellitic acid

2. HOOC—(CH₂)₄—COOR² ⟶

Mono(8-methylnonyl) adipate

R²OOC—(CH₂)₄—COOR² + HOOC—(CH₂)₄—COOH   (IV)
Bis(8-methylnonyl) adipate    Adipic acid In the above formulae, R¹ and R² represent $$-CH_2\overset{\underset{|}{C_2H_5}}{C}H(CH_2)_3CH_3 \text{ and } -CH_2(CH_2)_6\overset{\underset{|}{CH_3}}{C}HCH_3,$$

respectively.

It need hardly be said that alkali metal salts of half esters of polycarboxylic acids remaining in the ester treated and neutralized by the conventional methods deteriorate the electric insulation, transparency and thermal stability of the final ester.

Extensive studies on the basis of this finding led to the accomplishment of the present invention.

According to the present invention, there is provided a process for preparing esters which comprises reacting a polycarboxylic acid with an alcohol in the presence or absence of a catalyst, distilling off the unreacted alcohol from the esterification reaction mixture obtained to give a crude ester, heat-treating the crude ester at a temperature of 160° to 340° C. for 0.1 to 3 hours, contacting the heat-treated ester with an adsorbent at a temperature of 30° to 150° C. and then separating and recovering the desired ester from the crude ester.

The esterification reaction mixture in the present invention is obtained by an ordinary esterification reaction of a polycarboxylic acid with an alcohol, and contains the desired ester, the unreacted polycarboxylic acid, the unreacted alcohol, the half ester of polycarboxylic acid, and by-product water, traces of heavy metal salts, inorganic substances, and high-boiling substances, and sometimes the catalyst. The water formed as a result of the esterification reaction is mostly removed out of the reaction system as an azeotrope with the alcohol, and therefore, only a trace of it is present.

There is no particular limitation on the polycarboxylic acid used in this invention. Generally, examples of suitable polycarboxylic acids are aromatic polycarboxylic acids such as phthalic acid, isophthalic acid, terephthalic acid, nitrophthalic acid, aminophthalic acid, hemimellitic acid, trimellitic acid, trimesic acid, prehnitic acid, melophanic acid, pyromellitic acid, benzenepentacarboxylic acid, mellitic acid, and naphthalic acid; aliphatic saturated polycarboxylic acids such as oxalic acid, malonic acid, succinic acid, glutaric acid, adipic acid, ethylsuccinic acid, pimelic acid, ethylglutaric acid, suberic acid, azelaic acid, sebacic acid and brassylic acid; aliphatic unsaturated polycarboxylic acids such as maleic acid, fumaric acid, itaconic acid, mesaconic acid, citraconic acid and aconitic acid; hydroxycarboxylic acids such as malic acid, tartaric acid and citric acid; alicyclic polycarboxylic acids such as hexahydrophthalic acid, hexahydroisophthalic acid and hexahydroterephthalic acid; and anhydrides of these polycarboxylic acids. These polycarboxylic acids and acid anhydrides may be used as mixtures. Of these, the aromatic polycarboxylic acids, aliphatic saturated polycarboxylic acids and acid anhydrides of these are commercially preferred. Phthalic acid, isophthalic acid, terephthalic acid, trimellitic acid, anhydrides of these, and adipic acid are especially preferred.

No restriction is imposed either on the alcohols used in this invention. Generally, examples of suitable alcohols include aliphatic saturated monohydric alcohols such as methyl alcohol, ethyl alcohol, n-propyl alcohol, isopropyl alcohol, n-butyl alcohol, sec-butyl alcohol, tert-butyl alcohol, isobutyl alcohol, n-amyl alcohol, sec-amyl alcohol, tert-amyl alcohol, isoamyl alcohol, sec-isoamyl alcohol, active amyl alcohol, diethyl carbinol, tert-butyl carbinol, hexanol, heptanol, octanol, 2-ethylhexanol, nonanol, decanol, 8-methylnonanol, undecanol, dodecanol, and tridecanol; aliphatic saturated polyhydric alcohols such as ethylene glycol, diethylene glycol, propylene glycol, trimethylene glycol, tetramethylene glycol, 1,2-butanediol, 1,3-butanediol, 2,3-butanediol, 2,2-dimethyl-1,3-propanediol, glycerine, diglycerine, trimethylolpropane, pentaerythritol and dipentaerythritol; aliphatic unsaturated alcohols such as allyl alcohol, crotyl alcohol and propargyl alcohol; alicyclic alcohols such as cyclopentanol and cyclohexanol; alcohols containing an aromatic ring such as benzyl alcohol, β-phenyl ethyl alcohol, methyl phenyl carbinol, phthalyl alcohol and cinnamyl alcohol; heterocyclic alcohols such as furfuryl alcohol; and mixtures of these alcohols. Of these, aliphatic saturated monohydric alcohols containing 1 to 13 carbon atoms are especially preferred.

The esterification reaction proceeds either in the presence or absence of a catalyst. Where the catalyst is used, it may be an insoluble suspended catalyst for ordinary esterification reaction, examples of which are tin oxide, zinc oxide, antimony oxide, titanium peroxide, an alumina-sodium hydroxide mixed system, magnesium-silicon double oxide, sodium-aluminum double oxide, and magnesium-aluminum double oxide.

The half ester of polycarboxylic acid contained in the esterification reaction mixture means an ester of a polycarboxylic acid which contains at least one free carboxyl group. Examples of the half ester are a monoester of phthalic acid, a monoester of trimellitic acid, a diester of trimellitic acid, a triester of pyromellitic acid, and a monoester of adipic acid.

The unreacted alcohol is distilled off in a customary manner from the resulting esterification reaction mixture.

The crude ester, as referred to in the present application, is the ester which is obtained by distilling off the alcohol from the esterification reaction mixture, and contains impurities such as the polycarboxylic acid, the half ester of polycarboxylic acid, water, coloring substances, heavy metal salts, other inorganic substances, and sometimes the insoluble suspended catalyst.

The crude ester is heat-treated in accordance with the following procedures. The heat-treating temperature somewhat varies according to the type of the desired final ester, but should be from 160° to 340° C., preferably from 180° to 300° C. When the heat-treating temperature is lower than 160° C., the rate of double decomposition of the half ester to the desired ester as a final product and the polycarboxylic acid is very low to render the process infeasible. When it exceeds 340° C., the final ester undergoes saponification to become acidic, or is colored by heat decomposition.

The heat-treating time may be one sufficient for a greater part of the half ester of polycarboxylic acid to be double-decomposed. Preferably, it is shorter when the heat-treating temperature is higher, and longer when the temperature is lower. Commercially, periods of 0.1 to 3 hours are suitable although the time may be outside this range.

The pressure at the time of heat-treatment is not essential in the present invention, and may be elevated, atmospheric, or reduced. However, since the double decomposition of the half ester of polycarboxylic acid is an equilibrium reaction, it is preferred to perform the heat-treatment at reduced pressure so as to distill off the liberated polycarboxylic acid and promote the double decomposition.

In order to prevent the final ester from being colored by oxidation upon contact with air at elevated temperatures, the heat-treatment may be carried out while continuously or intermittently blowing a substantially inert gas, such as nitrogen, helium or carbon dioxide into the ester. The gas blown into the ester may be released into the outer atmosphere or re-used after purification. Preferably, the heat-treatment is carried out with forced stirring in order to render the temperature distribution of the ester uniform.

The substances contained in the heat-treated ester are the same as those contained in the crude ester, but contains a slightly smaller amount of the half ester of polycarboxylic acid, and larger amounts of both the polycarboxylic acid and the final ester. The heat-treated ester is sent to the adsorption step either as such or after removing the polycarboxylic acid. Preferably, the polycarboxylic acid is removed. In practice, the polycarboxylic acid is removed generally by distillation.

The heat-treated ester, either as such or after distillation of the polycarboxylic acid, is contacted with an adsorbent. The adsorption treatment may be carried out without distilling off the polycarboxylic acid. The polycarboxylic acid distilled off from the ester during the heat-treatment and the polycarboxylic acid distilled off from the heat-treated ester can be recovered for re-use in esterification.

The adsorbent used in this invention is a solid adsorbent which is not soluble in the final ester but causes the adsorption of acids thereof. Examples of the adsorbent are alkali metal oxides such as lithium oxide, sodium oxide, and potassium oxide; alkaline earth metal oxides such as magnesium oxide and calcium oxide; amphoteric oxides such as zinc oxide, cadmium oxide, boron oxide, aluminum oxide, gallium oxide, indium oxide, silicon oxide, germanium oxide, tin oxide, lead oxide, arsenic oxide, antimony oxide and bismuth oxide; other metal oxides having the ability to adsorb acids such as titanium oxide and iron oxide; metal hydroxides having the ability to adsorb acids such as titanium hydroxide, tin hydroxide, magnesium hydroxide and iron hydroxide; carbonates such as sodium carbonate, sodium bicarbonate, aluminum carbonate, magnesium carbonate and calcium carbonate; alkaline earth metal phosphates such as magnesium phosphate and calcium phosphate; amphoteric hydroxides such as aluminum hydroxide and silicon hydroxide; clay minerals such as bentonite and activated terra alba; diatomaceous earth; starch; anion exchange resins, zeolites; activated carbon; and mixtures of these substances having the ability to adsorb acids. Of these adsorbents, sodium oxide, magnesium oxide, aluminum oxide, silicon oxide, calcium oxide, and iron oxide, aluminum hydroxide, magnesium hydroxide, sodium carbonate, sodium bicarbonate, aluminum carbonate and magnesium carbonate are preferred. The adsorbent may be used in any of lump, granular or powder form.

The adsorption treatment temperature is 30° to 150° C. which is lower than the heat-treatment temperature. If it is lower than 30° C., the viscosity of the ester may increase to reduce the efficiency of solid-liquid contact. When it is higher than 150° C., the substance once adsorbed may be desorbed. The final ester formed may undergo saponification or may be colored by heat decomposition products. The time for the adsorption treatment varies according, for example, to the type of the polycarboxylic acid used, or the type of the adsorption treatment equipment, but generally it is not more than 5 hours.

The pressure at the time of the adsorption treatment may be elevated, normal atmospheric or reduced. The adsorbent may be dispersed in the heat-treated ester, or used as packed in an adsorption treatment tank. Where the adsorbent is used as dispersed in the ester, the adsorption treatment is preferably carried out with forced stirring in order to increase the efficiency of liquid-solid contact.

The amount of the adsorbent, in view of the essence of the present invention, may be one which is sufficient to cause the adsorption of the free polycarboxylic acid, the half ester of polycarboxylic acid, coloring substances, water, heavy metal salts and other inorganic substances (to be referred to simply as impurities such as polycarboxylic acid) contained in the heat-treated ester under stirring conditions at specified temperatures and pressures. The amount may vary according to the type of the apparatus used for adsorption, the types of impurities such as polycarboxylic acid, and the type of the adsorbent, but generally it is not more than 1/20, preferably from 1/1000 to 1/100, based on the weight of the ester heat-treated. Generally, the larger the amount of the adsorbent, the more complete is the adsorption of the impurities and the shorter is the time required for the adsorption treatment. If the amount of the adsorbent exceeds 1/20 of the weight of the ester heat-treated, the ester subjected to the adsorption treatment may sometimes become slurry-like, and lend itself to inconvenient handling in post-treatments such as filtration or sedimentation. Or because the amounts of the filtration cake and the sludge separated increase, the amount of the final ester which is lost as adhering to the filtration cake or carried by the sludge may increase. When the adsorbent is packed in an adsorption treatment tank, there is no particular limitation on the amount of the adsorbent. In other words, the adsorbent is replaced by a fresh one when it is exhausted.

The ester subjected to the adsorption treatment contains the final ester, the adsorbent and the impurities such as polycarboxylic acid adsorbed to the adsorbent, and sometimes the insoluble suspended catalyst.

The ester subjected to the adsorption treatment is separated into a first fraction, a final ester product, still residue a filtration cake, a sludge, etc. by distillation such as distillation at atmospheric pressure, steam distillation, distillation at reduced pressure, or vacuum distillation, and/or a solid-liquid separating means such as filtration, centrifugal separation or sedimentation. A flocculating agent may be used for centrifugal separation or sedimentation. The first fraction consists mainly of the substances having lower boiling points than the final ester (such as partly unadsorbed phthalic acid) and the final ester. The phthalic acid, etc. may be recovered for re-use in esterification. The final ester is of high purity. The still residue is a slurry which contains the adsorbent, and the impurities such as polycarboxylic acid adsorbed to the adsorbent, high boiling substances and a small amount of the final ester and sometimes, the insoluble suspended catalyst. The filtration cake results from the filtration of the ester subjected to the adsorption treatment, and is a wet cake containing the adsorbent, the impurities such as polycarboxylic acid adsorbed to the adsorbent, a small amount of the final ester adhering to them, and sometimes, the insoluble suspended catalyst. The sludge is a sludge obtained by separating from the supernatant liquid as the final ester by sedimentation or centrifugal separation, and contains the adsorbent, the impurities such as polycarboxylic acid adsorbed to the adsorbent, a small amount of the final ester, and sometimes, the flocculating agent and insoluble suspended catalyst.

The filtration cake is directly incinerated. The still residue and the separated sludge may be directly incinerated; or may be further filtered to obtain a filtration cake which is then incinerated. The final ester may be recovered from the filtrate obtained at this time.

The incineration temperature is usually 400° to 900° C., preferably 400° to 800° C., more preferably 450° to 650° C. The residual ash obtained by incineration may be re-used for the adsorption treatment. In an esterification reaction using an insoluble suspended catalyst, a part of the filtration cake, still residue, sludge or residual ash can be re-used as the catalyst. When the incineration temperature is lower than 400° C., organic substances contained in the filtration cake, still residue or separated sludge, such as the polycarboxylic acid and final ester, cannot be completed oxidized to carbon dioxide and water, but heat decomposition products remain in the residual ash with the result that the acid adsorbability or catalytic acitivity of the residual ash cannot be sufficiently revived. Or such decomposition products may cause contamination of the final ester when the residual ash is used as an adsorbent or an esterification catalyst. Temperatures exceeding 900° C. may cause a loss of the acid adsorbability and catalytic activity of the residual ash and render it infeasible for re-use.

When an insoluble suspended catalyst is used in the esterification reaction in the present invention, it is preferred to separate the catalyst from the esterification reaction mixture by a conventional solid-liquid separating means such as filtration, centrifugal separation or sedimentation before or after distilling off the unreacted alcohol from the esterification reaction mixture. The insoluble suspended catalyst separated is recovered, can be re-used for the esterification reaction.

The process of this invention can be performed continuously, semi-continuously, or batchwise.

The invention will be described in greater detail by reference to the accompanying drawings in which.

Figure 1:
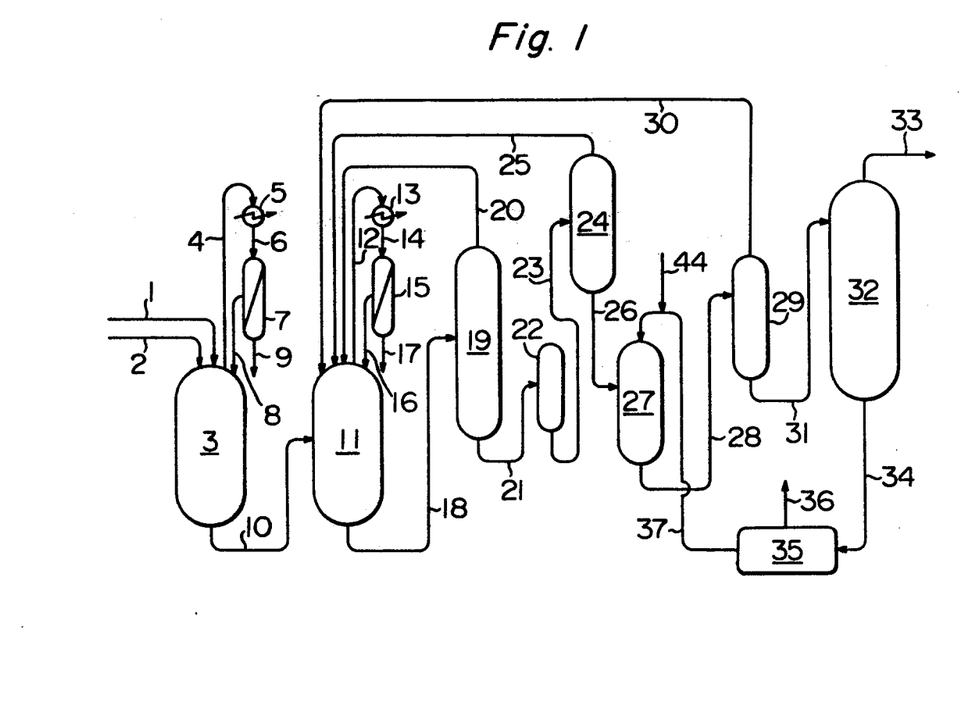
FIGS. 1 to 4 are flow sheets showing some embodiments of continuous esterification in accordance with the process of this invention.

Referring to FIG. 1, a polycarboxylic acid and an alcohol are fed through lines 1 and 2 respectively into a first esterification reactor 3 where they are esterified. The water formed as a result of esterification reaction is removed as an azeotrope with the alcohol, and the azeotrope supplied to a condenser 5 through a line 4. After condensation therein, it is sent to a decanter 7 through a line 6 and separated into an alcohol layer and an aqueous layer. The alcohol layer separated is returned to the first esterification reactor 3 through a line 8 and used again for the esterification reaction. Meanwhile, the aqueous layer separated is discharged out of the system through a line 9. The esterification reaction mixture withdrawn from the bottom of the first esterification reactor 3, the alcohol, the polycarboxylic acid, and the first fraction are fed into a second esterification reactor 11 through lines 10, 20, 25, and 30, respectively, and a further esterification reaction is carried out there. The water formed as a result of esterification in the second esterification reactor 11 is removed as an azeotrope with the alcohol. The azeotrope is sent to a condenser 13 through a line 12, and after condensation, sent to a decanter 15 through a line 14, where it is separated into an alcohol layer and an aqueous layer. The alcohol layer separated is returned through a line 16 to the second esterification reactor 11 for re-use in the esterification reaction. Meanwhile, the aqueous layer separated is discharged out of the system through a line 17. The esterification reaction mixture withdrawn from the bottom of the second esterification reactor 11 is sent to an alcohol distillation column 19 through a line 18 to distill off the unreacted alcohol. The alcohol withdrawn from the top of the alcohol distillation column 19 is sent to the second esterification reactor 11 through a line 20. On the other hand, the crude ester withdrawn from the bottom of the alcohol distillation column 19 is fed through a line 21 to a heating tank 22 where it is heat-treated. The ester heat-treated is supplied to an acid distillation column 24 through a line 23 to distill off the free polycarboxylic acid. The polycarboxylic acid withdrawn from the top of the acid distillation column 24 is returned through a line 25 to the second esterification reactor 11. The heat-treated ester withdrawn from the bottom of the acid distillation column 24 after distillation of the polycarboxylic acid therefrom is sent to an adsorbing tank 27 through a line 26, and the residual ash as an adsorbent is also fed to the adsorbing tank 27 through a line 37. Adsorption of impurities such as polycarboxylic acid is carried out in the adsorbing tank 27. As required, a fresh supply of adsorbent is fed to the adsorbing tank 27 through a line 44. The ester subjected to the adsorption treatment is withdrawn from the bottom of the adsorbing tank 27, and sent to a first rectifier 29 through a line 28 to distill off a first fraction consisting mainly of substances having lower boiling points than the final ester (e.g. partly unadsorbed phthalic acid) and a very small amount of final ester. The first fraction is withdrawn from the top of the first rectifier 29, and sent to the second esterification reactor 11 through a line 30. The ester from which the first fraction has been removed is withdrawn from the bottom of the first rectifier 29, and sent to a second rectifier 32 through a line 31, where it is purified by distillation at a high vacuum. The final ester is withdrawn from the top of the second rectifier 32, and recovered as a product through a line 33. The still residue is withdrawn from the bottom of the second rectifier 32, and sent to an incinerator 35 through a line 34 for incineration. Gases generated by the incineration treatment are released into the atmospheric air through a line 36. The residual ash is recovered at the incinerator 35, and sent to the adsorbing tank 27 through a line 37.

Figure 2:
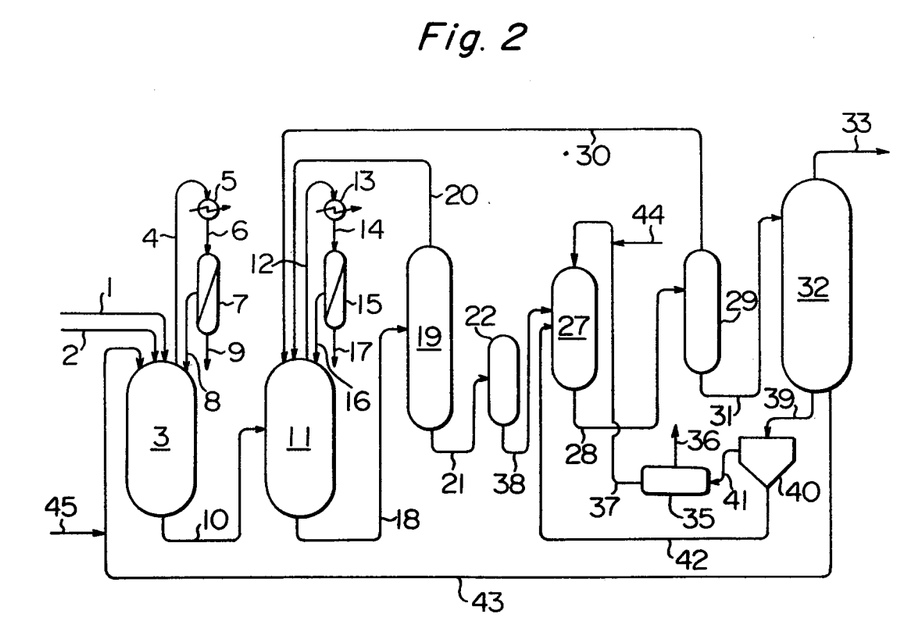

The method shown in FIG. 2 is a modification of the method shown in FIG. 1, in which the same substance as the adsorbent is used as an esterification reaction catalyst and the heat-treated ester is subjected to adsorption treatment without distilling off the polycarboxylic acid from it. Referring to FIG. 1, the reference numerals 1 to 22, 27 to 33, 35 to 37, and 44 and their functions are the same as those in FIG. 2. The heat-treated ester withdrawn from the bottom of the heating tank 22 is sent to the adsorbing tank 27 without distilling off the polycarboxylic acid, and subjected to adsorption treatment. A part of the still residue withdrawn from the second rectifier 32 is sent to a filter 40 through a line 39, and separated into a filtration cake and a filtrate. The cake is sent to the incinerator 35 through a line 41, and incinerated. The filtrate is returned to the adsorbing tank 27 through a line 42. The remainder of the still residue withdrawn from the bottom of the second rectifier 32 is sent to the first esterification reactor 3 through a line 43, and re-used as an esterification catalyst. If desired, a fresh supply of catalyst is fed through a line 45.

Figure 3:
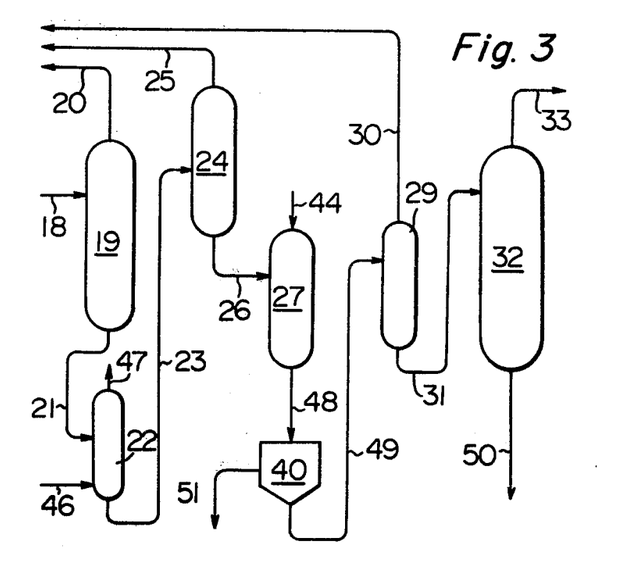

FIG. 3 is a flow sheet of another modification, in which the path from the feeding of the esterification reaction materials to the formation of the esterification reaction mixture is omitted. In FIG. 3, the esterification reaction mixture is fed to the alcohol distillation column 19 through the line 18 to distill off the unreacted alcohol. The alcohol is withdrawn from the top of the alcohol distillation column 19, and through the line 20, sent to an esterification reactor via an alcohol purification column for re-use in the esterification reaction. The crude ester withdrawn from the bottom of the alcohol distillation column 19 is sent to the heating tank 22 through the line 21. An inert gas is continuously fed into the heating tank 22 through a line 46, and discharged through a line 47. In the heating tank 22, the ester is heat-treated with forced stirring in an atmosphere of the inert gas. The heat-treated ester is withdrawn from the bottom of the heating tank 22, and through the line 23 sent to the acid distillation column 24 where the polycarboxylic acid is distilled off. The polycarboxylic acid withdrawn from the top of the acid distillation column 24 is sent to the esterification reactor through the line 25 for re-use in the preparation of esters. The ester withdrawn from the bottom of the acid distillation column 24 is sent to the adsorbing tank 27 through the line 26, and subjected to adsorption treatment with forced stirring. A solid adsorbent is fed to the adsorbing tank 27 through the line 44. The ester subjected the adsorption treatment and the adsorbent having adsorbed thereto the impurities are withdrawn from the bottom of the adsorbing tank 27, and sent to the filter 40 through a line 48. The ester subjected to the adsorption treatment is separated into a filtration cake and filtrate at the filter 40. The filtration cake is discharged out of the system through a line 51 or may be recovered and re-used. The filtrate is sent to the first rectifier 29 through a line 49. In the first rectifier 29, a first fraction consisting mainly of substances having lower boiling points than the final ester (e.g. partly unadsorbed phthalic acid) and a very small amount of final ester is withdrawn from the top of the first rectifier 29, and sent to the esterification reactor through the line 30 for re-use. The ester is withdrawn from the bottom of the first rectifier 29 and sent to the second rectifier 32 through the line 31, and purified by vacuum distillation. The final ester is withdrawn from the top of the second rectifier 32 through the line 33, and the still residue is discharged from the bottom through a line 50.

Figure 4:
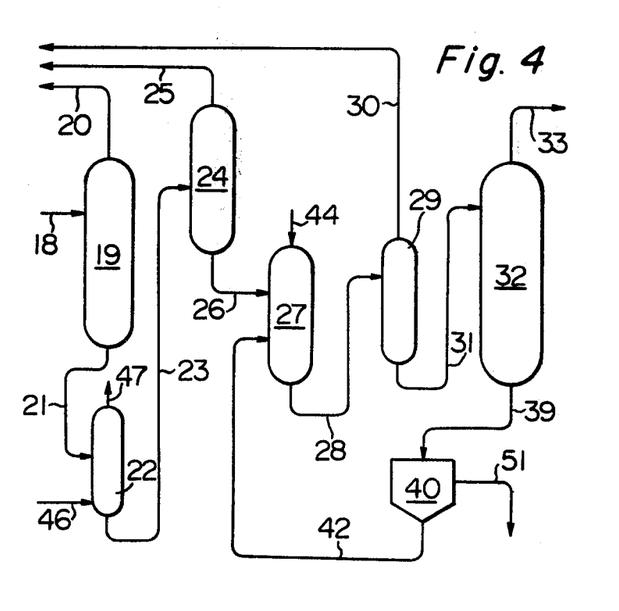

FIG. 4 is a flow sheet which shows a modification of the embodiment shown in FIG. 3, in which the crude ester subjected to the adsorption treatment is distilled without removing the adsorbent from it. The path up to the adsorption treatment is the same as in FIG. 3. In FIG. 4, the crude ester withdrawn from the bottom of the adsorbing tank 27 is sent to the first rectifier 29 without removing the adsorbent from it. The still residue withdrawn from the bottom of the second rectifier 32 is sent to the filter 40 through the line 39, and separated into a filtration cake and a filtrate. The filtration cake is discharged out of the system through a line 51 or may be recovered and re-used. The filtrate is returned to the adsorbing tank 27 through the line 42.

The process of this invention makes it possible to produce esters easily and efficiently by simple process steps without substantially discarding industrial wastes.

The water discharged from the reaction system in the process of this invention is only a small amount of clean water which is generated as a result of the esterification reaction, removed out of the reaction system as an azeotrope with the alcohol, and separated from the alcohol. According to the process of this invention, it is not necessary, as in the conventional processes, to neutralize or wash the esterification reaction mixture, and no great amount of water is positively used. Accordingly, the equipment for the production of esters can be small-sized. Moreover, there is no loss of the polycarboxylic acid and alcohol by dissolving, and no ester is carried away by the waste water. Hence, the reduction in the unit cost of ester production and the prevention of pollution by waste waters can be achieved simultaneously.

The esters produced by the method of this invention are substantially free from polycarboxylic acids, their half esters, their alkali metal salts, alkali metal salts of the half esters, water, coloring substances, heavy metal salts, and other inorganic substances. Accordingly, the esters have superior electric insulation, transparency and thermal stability, and are suitable as plasticizers for thermoplastic synthetic resins.

The following Examples and Comparative Examples further illustrate the present invention specifically. In these examples, all percentages and parts are by weight unless otherwise specified. The properties of the esters obtained in these examples determined in accordance with JIS K6751-1955 are tabulated at the end of the specification.

EXAMPLE 1

2-Ethylhexanol was distilled off at 50° C. and 0.5 mmHg from 1,506 parts of an esterification reaction mixture obtained by reacting phthalic anhydride with 2-ethylhexanol in the absence of catalyst and containing 74.19% of bis(2-ethylhexyl)phthalate, 2.49% of mono(2-ethylhexyl)phthalate and 23.30% of 2-ethylhexanol. The crude ester obtained was heat-treated with forced stirring at 180° to 190° C. under atmospheric pressure for 1.0 hour while blowing a nitrogen gas into it. To 1,151 parts of the heat-treated ester was added 2.0 parts of magnesium oxide as a solid adsorbent, and adsorption treatment was carried out with forced stirring at 80° C. under atmospheric pressure for 0.15 hour. The ester subjected to the adsorption treatment was purified by distillation at 0.1 to 0.2 mmHg, and a fraction boiling at 180° to 205° C. was recovered as a product. The resulting product, bis(2-ethylhexyl)phthalate, had high quality and superior thermal stability as tabulated hereinbelow.

EXAMPLE 2

1,485 Parts of an esterification reaction mixture obtained by reacting phthalic anhydride with Oxoalcohol 710 (a trademark for a product of Nissan Sekiyu Kagaku Co., Ltd., a mixed alcohol consisting of aliphatic saturated alcohols having 7 to 10 carbon atoms with a straight chain rate of 60%) using KYOWAAD 400 [a trademark for $Al(OH)_3.NaHCO_3$, a product of Kyowa Chemical Industry Co., Ltd.] and containing 78.71% of dialkyl phthalates, 0.01% of monoalkyl phthalates, 21.01% of the alcohol and 0.20% of KYOWAAD 400 was distilled at 65° to 70° C. and 0.3 mmHg to remove the alcohol. The resulting crude ester was heat-treated with forced stirring at 180° to 190° C. under atmospheric pressure for 1.0 hour while blowing a nitrogen gas into it. To 1,173 parts of the heat-treated ester was added 1.1 parts of a fresh supply of KYOWAAD 400 as a solid adsorbent, and adsorption treatment was performed with forced stirring at 80° C. under atmospheric pressure for 1.0 hour. A fraction boiling at 100° to 160° C. and 0.3 mmHg was distilled off from the ester subjected to the adsorption treatment. The still residue was filtered, and the resulting filtrate was recovered as a product.

The product, dialkyl phthalates, had high quality and superior thermal stability as tabulated hereinbelow.

EXAMPLE 3

1,435 Parts of an esterification reaction mixture obtained by reacting phthalic anhydride with Linevol 79 (a trademark for a product of Shell Chemical Co., which is a mixed alcohol consisting of aliphatic saturated alcohols containing 7 to 9 carbon atoms with a straight chain rate of 80%) using SEKADO KW (a trademark for $SiO_2.Al_2O_3.Fe_2O_3.CaO.MgO$, a product of Shinagawa Fire Brick Co., Ltd.) as a catalyst and containing 79.34% of dialkyl phthalates, 0.01% of monoalkyl phthalates, 20.36% of the alcohol and 0.19% of SEKADO KW was distilled at 62° to 66° C. and 0.3 to 0.4 mmHg to remove the alcohol. The resulting crude ester was heat-treated with forced stirring at 180° to 190° C. under atmospheric pressure for 1.0 hour while blowing a nitrogen gas into it. To 1,143 parts of the heat-treated ester was added 3.4 parts of a fresh supply of SEKADO KW as a solid adsorbent, and adsorption treatment was performed with forced stirring at 70° to 80° C. under atmospheric pressure for 1.0 hour. The ester subjected to the adsorption treatment was immediately purified by distilling at 0.1 to 0.2 mmHg, and a fraction boiling at 180° to 218° C. was recovered as a product.

The resulting product, dialkyl phthalates, had high quality and superior thermal stability as tabulated hereinbelow.

EXAMPLE 4

1,434 Parts of an esterification reaction mixture obtained by reacting isophthalic acid with 2-ethylhexanol using KYOWAAD 500 [a trademark for $Mg_6Al_2(OH)_{16}CO_3.4H_2O$, a product of Kyowa Chemical Industry Co., Ltd.] as a catalyst, and containing 80.60% of bis(2-ethylhexyl)isophthalate, 0.23% of mono(2-ethylhexyl)isophthalate, 19.02% of 2-ethylhexanol and 0.11% of KYOWAAD 500 was distilled at 50° to 62° C. and 0.4 to 0.5 mmHg to remove the 2-ethylhexanol. The resulting crude ester was heat-treated at 210° to 230° C. under atmospheric pressure for 1.0 hour with forced stirring while blowing a nitrogen gas into it. To 1,161 parts of a fresh supply of the heat-treated ester was added 5.4 parts of KYOWAAD 500 as a solid adsorbent, and the adsorption treatment was performed with forced stirring at 80° C. under atmospheric pressure for 1.0 hour. The ester subjected to the adsorption treatment was distilled at 0.5 mmHg to distill off a fraction boiling at 100° to 200° C. The still residue was filtered, and the resulting filtrate was recovered as a product.

The resulting product, bis(2-ethylhexyl)isophthalate, had high quality and superior thermal stability as tabulated hereinbelow.

EXAMPLE 5

1,244 Parts of an esterification reaction mixture obtained by reacting phthalic anhydride with 2-ethylhexanol using a mixture of KYOWAAD 400 with KYOWAAD 500 in a weight ratio of 3:1 as a catalyst and containing 94.00% of bis(2-ethylhexyl)phthalate, 0.06% of mono(2-ethylhexyl)phthalate, 5.64% of 2-ethylhexanol and 0.10% of the catalyst was distilled at 50° to 62° C. and 0.4 to 0.5 mmHg to remove the 2-ethylhexanol. The resulting crude ester was heat-treated at 190° to 210° C. for 0.5 hour under pressure of 1 to 3 mmHg with forced stirring. To 1,174 parts of the heat-treated ester was added a mixture of 0.9 part of KYOWAAD 400 and 0.3 part of KYOWAAD 500 as a solid adsorbent, and the adsorption treatment was carried out with forced stirring at 80° C. and atmospheric pressure for 0.5 hour. The ester subjected to the adsorption treatment was filtered, and the filtrate obtained was recovered as a product.

The product, bis(2-ethylhexyl)phthalate, had high quality and superior thermal stability as tabulated hereinbelow.

EXAMPLE 6

609 Parts of an esterification reaction mixture obtained by reacting trimellitic anhydride with 2-ethylhexanol using a mixture of aluminum hydroxide with sodium hydroxide in a weight ratio of 10:1 as a catalyst and containing 88.72% of tris(2-ethylhexyl)trimellitate, 1.02% of bis(2-ethylhexyl)trimellitate, 0.31% of mono(2-ethylhexyl)trimellitate, 9.10% of 2-ethylhexanol and 0.60% of the catalyst was distilled at 50° to 60° C. and 0.5 mmHg to remove the 2-ethylhexanol. The resulting crude ester was heat-treated with forced stirring at 320° to 325° C. and 1.5 kg/cm².G for 2.75 hours without blowing a nitrogen gas into it. The resulting heat-treated ester (554 parts) was simply distilled at 180° to 195° C. and 0.4 to 0.6 mmHg to remove a fraction consisting mainly of trimellitic acid formed as a result of double decomposition and being in an amount corresponding to 5% of the heat-treated ester. By adding 1.4 parts of a metal oxide of the composition $6MgO.Al_2O_3$ as a solid adsorbent, the ester was subjected to adsorption treatment with forced stirring at 140° C. under atmospheric pressure for 2.5 hours. The ester subjected to adsporption treatment was filtered at 10-20 mmHg using a glass filter having a pore size of 5 to 10 microns, and the filtrate obtained was recovered as a product.

The resulting product, tris(2-ethylhexyl)trimellitate, had high quality and superior thermal stability as tabulated hereinbelow.

EXAMPLE 7

488 Parts of an esterification reaction mixture obtained by reacting adipic acid with 8-methylnonanol in the absence of catalyst and containing 86.4% of bis(8-methylnonyl)adipate, 0.61% of mono(8-methylnonyl)adipate and 12.80% of 8-methylnonanol was distilled at 178° to 181° C. and 1.0 to 1.2 mmHg to remove the 8-methylnonanol. The resulting crude ester was heat-treated with forced stirring at 190° C. under atmospheric pressure for 0.75 hour while blowing a nitrogen gas into it. The heat-treated ester (426 parts) was simply distilled at 220° to 233° C. and 0.1 to 0.2 mmHg to remove 7.7%, based on the heat-treated ester, of a fraction consisting mainly of adipic acid formed as a result of double decomposition. The resulting ester was subjected to adsorption treatment with forced stirring at 110° C. under atmospheric pressure for 2.5 hours after adding 1.6 parts of a metallic oxide of the composition $6MgO \cdot Al_2O_3$ as an adsorbent. The ester subjected to the adsorption treatment was filtered at 10 to 30 mmHg through a glass filter having a pore size of 5 to 10 microns, and the filtrate was recovered as a product.

The resulting product, bis(8-methylnonyl)adipate, had high quality and superior thermal stability as tabulated hereinbelow.

EXAMPLE 8

The apparatus shown in FIG. 3 was used. 4,400.0 Parts of an esterification reaction mixture obtained by reacting phthalic anhydride with 2-ethylhexanol using a metal oxide of the composition $Na_2O \cdot Al_2O_3$ as a catalyst and containing 92.64% of bis(2-ethylhexyl)phthalate, 0.18% of mono(2-ethylhexyl)phthalate, 6.75% of 2-ethylhexanol, and 0.28% of the catalyst was fed hourly into alcohol distillation column 19 through conduit 18, and distilled to remove the 2-ethylhexanol while maintaining the column top temperature at 74° to 80° C. and the pressure of the inside of the column at 0.6 to 0.7 mmHg. The 2-ethylhexanol withdrawn from the top of alcohol distillation column 19 at a rate of 299.4 parts per hour was sent through conduit 20 to an esterification reactor via an alcohol purification column for re-use in the production of esters. The crude ester withdrawn from the bottom of alcohol distillation column 19 at a rate of 4,100.6 parts per hour was sent to heating tank 22 through conduit 21. A nitrogen gas was continuously fed into heating tank 22 through conduit 46, and discharged through conduit 47. In heating tank 22, the ester was heat-treated at 245° to 250° C. and 845 to 870 mmHg for 0.6 hour with forced stirring in an atmosphere of nitrogen. The heat-treated ester was withdrawn from the bottom of heating tank 22, and sent to acid distillation column 24 through conduit 23. In column 24, the phthalic anhydride was distilled off at a column top temperature of 130° to 145° C. and a pressure of 0.5 to 0.7 mmHg. The phthalic anhydride withdrawn from the top of acid distillation column 24 at a rate of 7.40 parts per hour was sent to the esterification reactor for re-use in the esterification reaction. The ester withdrawn from the bottom of acid distillation column 24 at a rate of 4,026.6 parts per hour was sent to adsorbing tank 27 through conduit 26, and subjected to adsorption treatment with forced stirring at 120° C. under atmospheric pressure for 1.5 hours. A metal oxide of the composition $Na_2O \cdot Al_2O_3$ was fed as an adsorbent into adsorbing tank 27 through conduit 44 at a rate of 16.1 parts per hour. The ester subjected to the adsorption treatment withdrawn from the bottom of the adsorbing column at a rate of 4,242.7 parts per hour was sent to filter 40 through conduit 48. The ester subjected to the adsorption treatment was separated into a small amount of a filtration cake and a filtrate at filter 40. The filtration cake was discharged out of the system through conduit 51, whereas the filtrate was sent to first rectifier 29 through conduit 49. At first rectifier 29, a first fraction consisting mainly of partly unadsorbed phthalic acid and a very small amount of bis(2-ethylhexyl)phthalate was distilled off at a column top temperature of 170° to 180° C. and a column inside pressure of 0.3 mmHg and withdrawn from the top of the column at a rate of 7.0 parts per hour. The first fraction was sent to the esterification reactor through conduit 30, and phthalic acid was re-used in the esterification reaction. The ester was withdrawn from the bottom of first rectifier 29, and sent to second rectifier 32 through conduit 31. In second rectifier 32, the ester was purified by distillation at a column top of 180° to 195° C. and a column inside pressure of 0.2 mmHg. The ester as a final product was withdrawn from the top of second rectifier 32 through conduit 33 at a rate of 4,084.1 parts per hour, and a small amount of the still residue was discharged from the bottom of the second rectifier 32 through conduit 50.

In the above manner, the ester was produced continuously for 21 days. The resulting product, bis(2-ethylhexyl)phthalate, had high quality and superior thermal stability as tabulated hereinbelow.

EXAMPLE 9

The apparatus shown in FIG. 3 was used. An esterification reaction mixture obtained by reacting phthalic anhydride with Linevol 911 (a trademark for a mixed alcohol consisting of aliphatic saturated alcohols having 9 to 11 carbon atoms with a straight chain rate of 60%, a product of Shell Chemical Co.) in the absence of a catalyst and containing 93.80% of dialkyl phthalates, 0.75% of monoalkyl phthalates and 5.08% of the alcohol was fed at a rate of 4.260.0 parts per hour into alcohol distillation column 19 through conduit 18, and distilled at a column top temperature of 90° to 92.5° C. and a column inside pressure of 0.4 to 0.5 mmHg to remove the alcohol. The alcohol withdrawn from the top of alcohol distillation column 19 at a rate of 216.5 parts per hour was sent to an esterification reactor via an alcohol purification column through conduit 20, and re-used for the esterification reaction. The crude ester withdrawn from the bottom of alcohol distillation column 19 at a rate of 4,043.5 parts per hour was sent to heating tank 22 through conduit 21, and heat-treated with forced stirring at 230° C. under atmospheric pressure for 0.75 hour without blowing an inert gas into it. The heat-treated ester was withdrawn from the bottom of heating tank 22, and sent to acid distillation column 24 through conduit 23. In column 24, phthalic anhydride was distilled off at a column top temperature of 150° C. and a pressure of 0.3 mmHg. Phthalic anhydride was withdrawn from the top of acid distillation column 24 at a rate of 10.73 parts per hour, and sent to the esterification reaction reactor through conduit 25 for re-use in the esterification reaction. The crude ester withdrawn from the bottom of acid distillation column 24 at a rate of 4,032.8 parts per hour was sent to adsorbing tank 27 through conduit 26, where it was subjected to adsorption treatment with forced stirring at 75° C. under atmospheric pressure for 0.5 hour. A metal oxide of the composition MgO.Al₂O₃ was fed as an adsorbent into the adsorbing tank 27 at a rate of 12.1 parts per hour through conduit 44. The ester subjected to adsorption treatment was withdrawn from the bottom of adsorption tank 27 at a rate of 4,044.9 parts per hour, and sent to filter 40 through conduit 48. The ester subjected to the adsorption treatment was separated in filter 40 into a small amount of a filtration cake and a filtrate. The filtration cake separated was discharged out of the system through conduit 51, and the filtrate was recovered as a product without purification by distillation.

The above procedure was continued for 14 days. The resulting product, dialkyl phthalates, had high quality and superior thermal stability as tabulated hereinbelow.

COMPARATIVE EXAMPLE 1

Example 1 was repeated except that the heat-treating step was omitted, and the ester subjected to adsorption treatment was divided into two portions, one of which was distilled without filtration, and the other of which was distilled after filtration.

In the case of directly distilling the adsorption-treated ester without filtration, needle-like white crystals began to deposit heavily in the vicinity of the top of the distillation column, when the temperature inside the distillation column exceeded 150° C. and the distillation ratio became 2% by volume. This resulted in pipe clogging, and it was impossible to continue the distillation. Analysis of the needle-like white crystals by an infrared spectrophotometer showed that the needles were phthalic anhydride.

In the case of distilling the filtrate of the ester, similar needle-like white crystals deposited in some amounts, but the distillation was not impeded and the final product was obtained. However, the bis(2-ethylhexyl) phthalate obtained had inferior quality and thermal stability to the product obtained in Example 1 as tabulated hereinbelow.

COMPARATIVE EXAMPLE 2

Example 2 was repeated except that the heat-treating step was omitted. The resulting product, dialkylphthalates, had inferior quality and thermal stability to the product obtained in Example 2 as tabulated hereinbelow.

COMPARATIVE EXAMPLE 3

Example 3 was repeated except that the heat-treating step was omitted. However, when the temperature of the inside of the rectifying column 32 exceeded 150° C. and the distillation ratio became 3% by volume, needle-like white crystals began to deposite heavily in the vicinity of the top of the distillation column. This resulted in pipe clogging, and it was impossible to continue the distillation. The needle-like white crystals were determined to be phthalic anhydride by analysis with an infrared spectrophotometer.

COMPARATIVE EXAMPLE 4

Example 4 was repeated except that the heat-treating step was omitted. The resulting product, bis(2-ethylhexyl)isophthalate, had inferior quality and thermal stability to the product obtained in Example 4 as tabulated hereinbelow.

COMPARATIVE EXAMPLE 5

Example 5 was repeated except that the heat-treating step was omitted. The resulting product, bis(2-ethylhexyl)phthalate, had inferior quality and thermal stability to the product obtained in Example 5 as tabulated hereinbelow.

COMPARATIVE EXAMPLE 6

Example 6 was repeated except that the heat-treating step was omitted. The resulting product, tris(2-ethylhexyl)trimellitate, had inferior quality and thermal stability to the product obtained in Example 6 as tabulated hereinbelow (see the column headed "after filtration").

The product obtained was distilled at 0.15 to 0.3 mmHg to remove a fraction boiling at 240° to 250° C. in an amount corresponding to 6% of the ester charged. The purified product obtained was much the same as the product obtained above, and had inferior quality and thermal stability as tabulated hereinbelow (see the column headed "after distillation").

COMPARATIVE EXAMPLE 7

Example 7 was repeated except that the heat-treating step was omitted. The product, bis(8-methylnonyl) adipate, had inferior quality and thermal stability to the product obtained in Example 7.

EXAMPLE 10

An esterification reaction mixture obtained by reacting 219.2 parts of adipic acid with 664.8 parts of 8-methylnonanol using 2.9 parts of a mixture of alumina and sodium hydroxide in a weight ratio of 10:1 at 195° to 215° C. under atmospheric pressure for 3.0 hours while removing water generated, and containing 74.11% of bis(8-methylnonyl)adipate, 0.11% of mono(8-methylnonyl)adipate, 25.31% of 8-methylnonanol and 0.45% of the catalyst was distilled at 175° to 180° C. and 1.0 to 1.5 mmHg to remove the unreacted 8-methylnonanol. The resulting crude ester was heat-treated for 2.5 hours at 286° C. and atmospheric pressure while blowing a dry nitrogen gas into it. From the heat-treated ester, free adipic acid was distilled off at 225° to 230° C. for 0.1 to 0.2 mmHg. The ester was subjected to adsorption treatment at 150° C. for 1.0 hour by adding 0.8%, based on the ester, of KYOWAAD 400. The hester subjected to the adsorption treatment was filtered, and separated into a filtrate and a filtration cake. The filtrate was distilled at 180° to 207° C. and 0.3 mmHg to remove a first fraction, and subsequently distilled at 4 mmHg to afford a fraction boiling at 240° to 247° C. which was recovered as product I, i.e., bis(8-methylnonyl)adipate. 10.7 Parts of the resulting still residue was divided into two portions. One portion (6.8 parts) was incinerated at 600° C. to afford 5.1 parts of a residual ash.

The remainder (3.9 parts) of the distillation bottoms was used as a catalyst for the esterification reaction, and otherwise under the same conditions as set forth above, an esterification reaction mixture containing 74.89% of bis(8-methylnonyl)adipate, 0.12% of mono(8-methylnonyl)adipate, 24.36% of 8-methylnonanol and 0.50% of the catalyst was obtained. The esterification reaction mixture so obtained was treated in the same way as set forth above except that 5.1 parts of the residual ash was used as the adsorbent. Thus, bis(8-methylnonyl)adipate was obtained as a product II.

The products I and II had high quality and superior thermal stability as tabulated hereinbelow.

EXAMPLE 11

An esterification reaction mixture obtained by reacting 207.5 parts of isophthalic acid and 508.4 parts of n-amyl alcohol at 220° to 250° C. under atmospheric pressure for 7.0 hours using 9.0 parts of KYOWAAD 500 as a catalyst, and containing 65.37% of diamyl isophthalate, 0.08% of monoamyl isophthalate, 31.67% of n-amyl alcohol and 0.06% of the catalyst was distilled at 80° to 100° C. and 1.0 to 2.0 mmHg to remove the unreacted n-amyl alcohol. The resulting crude ester was heat-treated for 1.0 hour at 160° C. under atmospheric pressure while blowing a dry nitrogen gas into it. The heat-treated ester, without distilling off the free isophthalic acid, was subjected to adsorption treatment at 60° C. for 0.5 hour after adding 0.5%, based on the heat-treated ester, of KYOWAAD 500. The ester subjected to the adsorption treatment was distilled at 0.5 mmHg without filtration beforehand to remove a first fraction boiling at 110° to 130° C., and subsequently distilled at 0.2 to 0.4 mmHg to afford a fraction boiling at 175° to 210° C. as a product I (diamyl isophthalate).

The resulting still residue (17.9 parts) was divided into two portions. One portion (3.6 parts) was incinerated at 550° C. to afford 2.3 parts of a residual ash.

Under the same conditions as above except that the remainder (14.3 parts) of the still residue was used as the esterification catalyst, an esterification reaction mixture containing 65.51% of diamyl isophthalate, 0.10% of monoamyl isophthalate, 32.30% of n-amyl alcohol and 2.05% of the catalyst was obtained. The reaction mixture was treated in the same manner as set forth above except that 2.3 parts of the residual ash was used as the adsorbent. Diamyl isophthalate was obtained as a product II.

The products I and II both had high quality and superior thermal stability as tabulated hereinbelow.

EXAMPLE 12

An esterification reaction mixture obtained by reacting 288.2 parts of trimellitic anhydride with 1015.0 parts of 2-ethylhexanol at 200° to 235° C. under atmospheric pressure for 3.5 hours using 18.8 parts of KYOWAAD 400 as a catalyst, and containing 63.74% of tris(2-ethylhexyl) trimellitate, 0.39% of bis(2-ethylhexyl)trimellitate, 0.32% of mono(2-ethylhexyl)trimellitate, 33.62% of 2-ethylhexanol, and 1.85% of the catalyst was distilled at 50° to 60° C. and 0.4 mmHg to remove the unreacted 2-ethylhexanol. The resulting crude ester was heat-treated at 305° C. and 1.35 kg/cm$^2$.G for 2.0 hours without blowing an inert gas into it. The heat-treated ester, without distilling off the free trimellitic acid, was subjected to adsorption treatment at 145° C. for 1.0 hour after adding 0.9%, based on the heat-treated ester, of KYOWAAD 400 as an adsorbent. The ester subjected to the adsorption treatment was distilled at 0.5 to 1.0 mmHg to distill off a first fraction boiling at 165° to 180° C., and subsequently filtered at 150° C. and 1.0 mmHg through a glass filter having a pore size of 5 to 10 microns. The filtrate was recovered as a product I [i.e., tris(2-ethylhexyl)trimellitate]. The resulting filtration cake (32.8 parts) was divided into two portions. One portion (9.3 parts) was incinerated at 450° C. to afford 7.4 parts of a residual ash.

The other portion (23.5 parts) of the cake was used as an esterification reaction catalyst, and otherwise, the same procedure as above was repeated to afford an esterification reaction mixture consisting of 63.55% of tris(2-ethylhexyl)trimellitate, 0.51% of bis(2-ethylhexyl)trimellitate, 0.32% of mono(2-ethylhexyl)trimellitate, 33.69% of 2-ethylhexanol, and 1.90% of the catalyst. The reaction mixture was treated in the same way as set forth above except that 7.4 parts of the residual ash was used as the adsorbent. This (2-ethylhexyl)trimellitate was obtained as a product II.

The products I and II had high quality and superior thermal stability as tabulated hereinbelow.

EXAMPLE 13

The apparatus shown in FIG. 1 was used. Phthalic anhydride and 2-ethylhexanol were fed into first esterification reactor 3 at a rate of 1,406.0 parts per hour and 2,470.0 parts per hour respectively through conduits 1 and 2. In first esterification reactor 3, esterification was performed in the absence of catalyst at 170° to 180° C. under atmospheric pressure. Water generated as a result of the esterification reaction was removed as an azeotrope with 2-ethylhexanol, and the azeotrope sent through conduit 4 to condenser 5 where it was condensed. The mixture was sent to decanter 7 through conduit 6, and separated into 2-ethylhexanol and water. The 2-ethylhexanol separated was returned to first esterification reactor 3 through conduit 8, and re-used for the esterification. On the other hand, the separated clean water was discharged out of the reaction system through conduit 9. The esterification reaction mixture withdrawn from the bottom of the reactor 3 at a rate of 3,787.0 parts per hour, 2-ethylhexanol recovered from alcohol distillation column 19 at a rate of 1,230.0 parts per hour, the polycarboxylic acid recovered from acid distillation column 24 at a rate of 29.2 parts in total per hour, and the first fraction recovered from first rectifier 29 at a rate of 8.5 parts per hour were fed into second esterification reactor 11 respectively through conduits 10, 20, 25, and 30. In the second esterification reactor 11, esterification reaction was further performed in the absence of catalyst at 220° to 250° C. under atmospheric pressure. Water generated as a result of the esterification reaction was removed as an azeotrope with 2-ethylhexanol, which was then sent to condenser 13 through conduit 12 and condensed. The resultant mixture was sent to decanter 15 through conduit 14 and separated into 2-ethylhexanol and water. The 2-ethylhexanol separated was returned to second esterification reactor 11 through conduit 16 for re-use in the esterification reaction. On the other hand, water separated was discharged out of the reaction system through conduit 17. The esterification reaction mixture withdrawn from the bottom of the second esterification reactor 11 at a rate of 4,976.0 parts per hour was sent to alcohol distillation column 19 through conduit 18, and free 2-ethylhexanol was distilled off at 50° to 60° C. and 0.4 mmHg. The 2-ethylhexanol withdrawn from the top of alcohol distillation column 19 at a rate of 1,230.0 parts per hour was returned to second esterification reactor 11 through conduit 20, and re-used for the esterification. The crude ester withdrawn from the bottom of alcohol distillation column 19 at a rate of 3,746 parts per hour was sent to heating tank 22 through conduit 21, and heat-treated with forced stirring at 200° C. under atmospheric pressure with an average residence time of 0.75 hour without blowing an inert gas into it.

The heat-treated ester was sent to acid distillation column 24 through conduit 23 at a rate of 3,746.0 parts per hour, and free phthalic acid was distilled off at 140° to 160° C. and 0.2 to 0.4 mmHg. Phthalic acid was withdrawn from the top of acid distillation column 24 at a rate of 29.2 parts in total per hour, and returned to second esterification reactor 11 through conduit 25. The heat-treated ester withdrawn from the bottom of acid distillation column 24 at a rate of 3,716.8 parts per hour after distillation of the phthalic acid, and the residual ash of the composition $MgO.Al_2O_3$ recovered at a rate of 5.8 parts per hour from incineration furnace 35 were fed into adsorbing tank 27 through conduit 26, and screw conveyor 37, respectively. In the adsorbing tank 27, the adsorption treatment was performed with forced stirring at 80° C. under atmospheric pressure for 0.5 hour. The ester subjected to the adsorption treatment was withdrawn from the bottom of adsorbing tank 27 at a rate of 3,722.6 parts per hour, and sent to first rectifier 29 through conduit 28, and at 140° to 175° C. and 0.2 mmHg, a first fraction consisting mainly of substances having lower boiling points than the desired bis(2-ethylhexyl)phthalate (such as phthalic acid) and a very small amount of bis(2-ethylhexyl)phthalate was distilled off. The first fraction withdrawn from the top of first rectifier 29 at a rate of 8.5 parts per hour was returned to second esterification reactor 11 through conduit 30, and re-used in the esterification reaction. The ester from which the first fraction had been removed was withdrawn from the bottom of first rectifier 29 at a rate of 3,714.1 parts per hour, and sent to second rectifier 32 through conduit 31. In second rectifier 32, it was purified by distillation at 0.1 to 0.3 mmHg. A fraction boiling at 185° to 205° C. was withdrawn from the top of second rectifier 32 at a rate of 3,679.1 parts per hour, and recovered as a product through conduit 33.

On the other hand, the still residue was withdrawn from the bottom of second rectifier 32 at a rate of 35.0 parts per hour, and sent to incinerator 35 through conduit 34, where it was incinerated at 800° C. A gas consisting mainly of carbon dioxide and steam generated in the incinerator 35 was released into the atmospheric air through conduit 36. The residual ash obtained by the incineration treatment was recovered at a rate of 5.8 parts per hour, and sent to adsorbing tank 27 through screw conveyor 37, and re-used for adsorption treatment.

The above procedure was continued for 18 days. The resulting product, bis(2-ethylhexyl)phthalate, had high quality and superior thermal stability as tabulated hereinbelow.

EXAMPLE 14

The procedure of Example 13 was continued for 11 days except as noted below.

Diadol 711L (a trademark for a mixed alcohol consisting of aliphatic saturated alcohols having 7, 9 and 11 carbon atoms with a straight chain rate of 50%, a product of Mitsubishi Chemical Industries Limited) was used instead of 2-ethylhexanol; the esterification reaction temperatures at the first reactor 3 and the second reactor 11 were changed to 170°–185° and 200°–245° C., respectively; the pressure and distilling temperature at alcohol distillation column 19 were changed to 0.5 mmHg and 50°–100° C.; the average residence time in heating tank 22 was changed to 1.0 hour; a dry nitrogen gas was blown into the ester during heat treatment; KYOWAAD 300 (a trademark for a product of Kyowa Chemical Industry Co., Ltd. having the composition 2.5 $MgO.Al_2O_3.xH_2O$) regenerated by incineration was used in an amount of 0.23% based on the ester for the adsorption treatment; the temperature and average residence time in adsorbing tank 27 were changed to 100° C., and 1.0 hour; the distilling temperature in first rectifier 29 was changed to 140° to 170° C.; the pressure and distilling temperature in second rectifier 32 were changed to 0.1–0.2 mmHg and 185°–220° C.; and the temperature for incineration in the incinerator 35 was changed to 750° C.

The product, dialkyl phthalates, had high quality and superior thermal stability as tabulated hereinbelow.

EXAMPLE 15

The procedure of Example 13 was continued for 23 days except as noted below.

Linevol 79 was used instead of 2-ethylhexanol; the esterification reaction temperatures in the first reactor 3 and second reactor 11 were changed to 160°–175° C. and 195°–230° C., respectively; the pressure and distilling temperature in alcohol distillation column 19 were changed to 0.5 mmHg and 50°–95° C.; the temperature and average residence time in heating tank 22 were changed to 205° C. and 1.0 hour; the pressure and distilling temperature in acid distillation column 24 were changed to 0.2–0.3 mmHg and 135°–160° C.; KYOWAAD 300 regenerated by an incineration treatment was used as an adsorbent in an amount of 0.21% based on the heat-treated ester; the temperature and average residence time in adsorbing tank 27 were changed to 100° C. and 1.0 hour; the distilling temperature in first rectifier 29 was changed to 140°–170° C.; and the pressure and distilling temperature in second rectifier 32 were changed to 0.1–0.2 mmHg and 190°–210° C.

The apparatus shown in FIG. 2 was used.

The resulting product, dialkyl phthalates, had high quality and superior thermal stability as tabulated hereinbelow.

EXAMPLE 16

The procedure of Example 14 was continued for 10 days except as noted below.

Diadol 711L was used instead of Oxoalcohol 710; a part of the still residue withdrawn from the bottom of second rectifier 32 was used as a catalyst for esterification reaction in accordance with the flow sheet of FIG. 2; the esterification temperature and time in first esterification reactor 3 were changed to 160°–180° C. and 2.2 hours; the esterification temperature in second esterification reactor 11 was changed to 190°–240° C.; the distilling temperature at alcohol distillation column 19 was changed to 60°–100° C.; the temperature in heating tank 22 was changed to 210° C.; the heat-treated ester was directly sent to adsorbing tank 27 through conduit 38 without going through an acid distillation column; SEKADO KW regenerated by incineration at 630° C. was used as an adsorbent in an amount of 0.26% based on the heat-treated ester; the temperature in adsorbing tank 27 was changed to 80° C.; the pressure and distilling temperature in first rectifier 29 was changed to 0.4 mmHg and 130°–180° C.; the pressure and distilling temperature in second rectifier 32 were changed to 0.2 mmHg and 190°–218° C.; a part of the still residue withdrawn from the bottom of second rectifier 32 was sent to filter 40 through conduit 39 to separate it into a filtration cake and a filtrate, after which the filtration cake was sent to incinerator 35 through conduit 41 and incinerated at 630° C. for re-use as an adsorbent, whereas the filtrate was sent to adsorbing tank 27 to recover the final ester from it; and the remainder of the still residue withdrawn from the bottom of second rectifier 32 was sent to first esterification reactor 3 through conduit 43 and re-used as the esterification catalyst.

The resulting product, dialkyl phthalates, had high quality and superior thermal stability as tabulated hereinbelow.

COMPARATIVE EXAMPLE 8

An ester was produced using still residue and a residual ash in the same way as in Example 10 except that the heat-treating step was omitted. The resulting product, bis(8-methylnonyl)adipate, had inferior quality and thermal stability to the products I and II obtained in Example 10 as tabulated hereinbelow.

COMPARATIVE EXAMPLE 9

An ester was produced using still residue and a residual ash in the same way as in Example 11 except that the heat-treating step was omitted. The resulting product, diamyl isophthalate, had inferior quality and thermal stability to the products I and II obtained in Example 11 as tabulated hereinbelow.

COMPARATIVE EXAMPLE 10

An ester was produced using a filtration cake and a residual ash in the same way as in Example 12 except that the heat-treating step was omitted. The resulting product, tris(2-ethylhexyl)trimellitate, had inferior quality and thermal stability to the products I and II obtained in Example 12 as tabulated hereinbelow.

COMPARATIVE EXAMPLE 11

An ester was produced by using the still residue and the residual ash in the same way as in Example 11 except that the heat-treatment was carried out at 125° C. for 10 hours. The resulting diamyl isophthalate was inferior to Products I and II of Example 11, and had extremely low thermal stability as tabulated hereinbelow.

COMPARATIVE EXAMPLE 12

The procedure of Example 13 was repeated except that the adsorption treatment was performed at 28° C. The resulting bis(2-ethylhexyl)phthalate (product A) was far inferior to the product of Example 13 as tabulated hereinbelow.

Separately, the procedure of Example 13 was repeated except that the adsorption treatment temperature was changed to 28° C., the amount of the adsorbent was changed to 15 parts/hr, and the adsorption time (average residence time) was changed to 2.5 hours.

The resulting bis(2-ethylhexyl)phthalate (product B) was still inferior to the product of Example 13.

COMPARATIVE EXAMPLE 13

The procedure of Example 3 was repeated except that the heat-treatment temperature was changed to 360° C.

The resulting dialkyl phthalate had far inferior thermal stability to the product of Example 3 as tabulated hereinbelow.

COMPARATIVE EXAMPLE 14

The procedure of Example 8 was repeated except that the heat-treatment temperature was changed to 355° C., and the adsorption treatment temperature was changed to 25° C.

The resulting bis(2-ethylhexyl)phthalate had far inferior thermal stability to the product of Example 8 as tabulated hereinbelow.

COMPARATIVE EXAMPLE 15

The procedure of Example 5 was repeated except that the adsorption treatment step was omitted.

The resulting bis(2-ethylhexyl)phthalate (product I) had far inferior thermal stability to the product of Example 5 as tabulated hereinbelow.

The crude ester obtained after the heat-treatment was distilled to form a final ester (product II). Product II also had far inferior thermal stability to the product of Example 5 as tabulated hereinbelow.

COMPARATIVE EXAMPLE 16

The procedure of Example 13 was repeated except that the adsorption treatment was omitted.

The resulting bis(2-ethylhexyl)phthalate had far inferior thermal stability to the product of Example 13 as tabulated hereinbelow.

COMPARATIVE EXAMPLE 17

The procedure of Example 13 was repeated except that the adsorption treatment temperature was changed to 180° C.

The resulting bis(2-ethylhexyl)phthalate had far inferior thermal stability to the product of Example 13 as tabulated hereinbelow.

COMPARATIVE EXAMPLE 18

The procedure of Example 13 was repeated except that the heat-treatment temperature was changed to 175° C., and the adsorption treatment temperature was changed to 180° C.

The resulting bis(2-ethylhexyl)phthalate had far inferior thermal stability to the product of Example 13 as tabulated hereinbelow.

COMPARATIVE EXAMPLE 19

The procedure of Example 7 was repeated except that the heat-treatment temperature was changed to 140° C., and the adsorption treatment temperature was changed to 160° C.

The resulting product had far inferior thermal stability to the product of Example 7 as tabulated hereinbelow.

COMPARATIVE EXAMPLE 20

The procedure of Example 13 was repeated except that the heat-treatment temperature was changed to 360° C., and the adsorption treatment temperature was changed to 180° C.

The resulting bis(2-ethylhexyl)phthalate had far inferior thermal stability to the product of Example 13 as tabulated hereinbelow.

COMPARATIVE EXAMPLE 21

The procedure of Example 8 was repeated except that the heat-treatment temperature was changed to 145° C., and the adsorption treatment temperature was changed to 25° C.

The resulting bis(2-ethylhexyl)phthalate had far inferior thermal stability to the product of Example 8 as tabulated hereinbelow.

|  | Example 1 | Example 2 | Example 3 | Example 4 | Example 5 | Example 6 | Example 7 |
|---|---|---|---|---|---|---|---|
| Hazen Number (A.P.H.A. method) | below 10 | 15 | 10 | 15 | 10 | 15 | 10 |
| Acid Value (mg KOH/g) | 0.007 | 0.021 | 0.009 | 0.019 | 0.023 | 0.021 | 0.010 |
| Ester Value (mg KOH/g) | 288 | 288 | 294 | 288 | 288 | 307 | 262 |
| Volume specific resistance at 30° C. ($\Omega \cdot cm$) | $9.0 \times 10^{11}$ | $7.0 \times 10^{12}$ | $6.2 \times 10^{12}$ | $1.0 \times 10^{12}$ | $5.8 \times 10^{11}$ | $6.2 \times 10^{11}$ | $1.3 \times 10^{12}$ |
| Weight loss after heating at 125° C. for 3 hours (%) | 0.05 | 0.08 | 0.08 | 0.06 | 0.10 | 0.10 | 0.04 |
| Acid value after heating at 200° C. for 24 hours (mg KOH/g) | 0.010 | 0.030 | 0.030 | 0.051 | 0.042 | 0.029 | 0.017 |
| Hazen number after heating at 200° C. for 24 hours (A.P.H.A. method) | 10 | 25 | 15 | 20 | 20 | 20 | 10 |

|  | Example 8 | Example 9 | Comparative Example 1 | Comparative Example 2 | Comparative Example 4 | Comparative Example 5 |
|---|---|---|---|---|---|---|
| Hazen Number (A.P.H.A. method) | below 10 | below 10 | 15 | 15 | 15 | 10 |
| Acid Value (mg KOH/g) | 0.015 | 0.021 | 0.151 | 0.182 | 0.410 | 0.025 |
| Ester Value (mg KOH/g) | 288 | 249 | 288 | 288 | 287 | 288 |
| Volume specific resistance at 30+ C. ($\Omega \cdot cm$) | $7.8 \times 10^{11}$ | $9.0 \times 10^{11}$ | $5.8 \times 10^{10}$ | $8.1 \times 10^{10}$ | $1.5 \times 10^{9}$ | $7 \times 10^{10}$ |
| Weight loss after heating at 125° C. for 3 hours (%) | 0.08 | 0.07 | 0.65 | 0.51 | 0.70 | 0.14 |
| Acid value after heating at 200° C. for 24 hours (mg KOH/g) | 0.020 | 0.039 | 0.358 | 0.438 | 1.231 | 0.670 |
| Hazen number after heating at 200° C. for 24 hours (A.P.H.A. method) | 10 | 15 | 25 | 30 | 40 | 40 |

|  | Comparative Example 6 | | Comparative Example 7 | Example 10 | | Example 11 | |
|---|---|---|---|---|---|---|---|
|  | After filtration | After distillation |  | Product I | Product II | Product I | Product II |
| Hazen Number (A.P.H.A. method) | 15 | 10 | 10 | 10 | 10 | below 10 | below 10 |
| Acid Value (mg KOH/g) | 0.022 | 0.078 | 0.021 | 0.019 | 0.010 | 0.015 | 0.015 |
| Ester Value (mg KOH/g) | 305 | 306 | 261 | 263 | 263 | 309 | 309 |
| Volume specific resistance at 30° C. ($\Omega \cdot cm$) | $5.2 \times 10^{10}$ | $9.0 \times 10^{10}$ | $4.3 \times 10^{10}$ | $7.0 \times 10^{11}$ | $8.0 \times 10^{11}$ | $9.7 \times 10^{11}$ | $1.8 \times 10^{12}$ |
| Weight loss after heating at 125° C. for 3 hours (%) | 0.15 | 0.10 | 0.202 | 0.06 | 0.05 | 0.05 | 0.04 |
| Acid value after heating at 200° C. for 24 hours (mg KOH/g) | 0.424 | 0.191 | 0.452 | 0.030 | 0.031 | 0.020 | 0.017 |
| Hazen number after heating at 200° C. for 24 hours (A.P.H.A. method) | 100 | 60 | 180 | 25 | 15 | 15 | 10 |

|  | Example 12 | | Example 13 | Example 14 | Example 15 | Example 16 | Comparative Example 8 |
|---|---|---|---|---|---|---|---|
|  | Product I | Product II |  |  |  |  |  |
| Hazen Number (A.P.H.A. method) | below 10 | below 10 | below 10 | below 10 | below 10 | below 10 | 15 |
| Acid Value (mg KOH/g) | 0.020 | 0.020 | 0.003 | 0.001 | 0.008 | 0.010 | 0.032 |
| Ester Value (mg KOH/g) | 306 | 306 | 287 | 286 | 295 | 288 | 261 |
| Volume specific resistance at 30° C. ($\Omega \cdot cm$) | $7.7 \times 10^{11}$ | $1.1 \times 10^{12}$ | $2.8 \times 10^{12}$ | $7.9 \times 10^{11}$ | $6.5 \times 10^{11}$ | $4.7 \times 10^{11}$ | $3.0 \times 10^{9}$ |
| Weight loss after |  |  |  |  |  |  |  |

| -continued | | | | | | | |
|---|---|---|---|---|---|---|---|
| heating at 125° C. for 3 hours (%) | 0.05 | 0.05 | 0.04 | 0.05 | 0.09 | 0.06 | 0.96 |
| Acid value after heating at 200° C. for 24 hours (mg KOH/g) | 0.030 | 0.025 | 0.009 | 0.007 | 0.015 | 0.029 | 1.202 |
| Hazen number after heating at 200° C. for 24 hours (A.P.H.A. method) | 10 | below 10 | below 10 | below 10 | 10 | 15 | 50 |

| | Comparative Example 9 | Comparative Example 10 | Comparaive Example 11 | Comparative Example 12 Product A | Comparative Example 12 Product B | Comparative Example 13 |
|---|---|---|---|---|---|---|
| Hazen Number (A.P.H.A. method) | 15 | 40 | below 10 | 20 | 15 | 40 |
| Acid Value (mg KOH/g) | 0.281 | 0.061 | 0.252 | 0.630 | 0.248 | 0.745 |
| Ester Value (mg KOH/g) | 307 | 305 | 309 | 286 | 287 | 293 |
| Volume specific resistance at 30° C. ($\Omega \cdot$ cm) | $5.5 \times 10^{10}$ | $7.0 \times 10^9$ | $4.0 \times 10^9$ | $5.0 \times 10^{10}$ | $3.1 \times 10^{11}$ | $1.0 \times 10^{11}$ |
| Weight loss after heating at 125° C. for 3 hours (%) | 0.06 | 1.40 | 0.75 | 0.32 | 0.10 | 0.20 |
| Acid value after heating at 200° C. for 24 hours (mg KOH/g) | 1.520 | 2.110 | 0.650 | 1.410 | 0.311 | 1.102 |
| Hazen number after heating at 200° C. for 24 hours (A.P.H.A. method) | 250 | 150 | 60 | 40 | 20 | 60 |

| | Comparative Example 14 | Comparative Example 15 Product I | Comparative Example 15 Product II | Comparative Example 16 | Comparative Example 17 | Comparative Example 18 |
|---|---|---|---|---|---|---|
| Hazen Number (A.P.H.A. method) | 65 | 70 | 15 | 50 | 20 | 25 |
| Acid Value (mg KOH/g) | 0.510 | 0.487 | 0.118 | 0.261 | 0.123 | 0.110 |
| Ester Value (mg KOH/g) | 287 | 286 | 287 | 286 | 287 | 287 |
| Volume specific resistance at 30° C. ($\Omega \cdot$ cm) | $6.2 \times 10^{10}$ | $4.0 \times 10^{10}$ | $7.9 \times 10^{10}$ | $8.3 \times 10^9$ | $7.5 \times 10^{10}$ | $7.4 \times 10^{10}$ |
| Weight loss after heating at 125° C. for 3 hours (%) | 0.18 | 0.35 | 0.14 | 0.34 | 0.28 | 0.24 |
| Acid value after heating at 200° c. for 24 hours (mg KOH/g) | 0.980 | 0.721 | 0.285 | 0.411 | 0.316 | 0.303 |
| Hazen number after heating at 200° C. for 24 hours (A.P.H.A. method) | 80 | 100 | 25 | 60 | 40 | 30 |

| | Comparative Example 19 | Comparative Example 20 | Comparative Example 21 |
|---|---|---|---|
| Hazen Number (A.P.H.A. method) | 15 | 40 | 15 |
| Acid Value (mg KOH/g) | 0.150 | 0.450 | 0.188 |
| Ester Value (mg KOH/g) | 261 | 287 | 287 |
| Volume specific resistance at 30° C. ($\Omega \cdot$ cm) | $1.0 \times 10^{11}$ | $4.8 \times 10^{10}$ | $5.9 \times 10^{10}$ |
| Weight loss after heating at 125° C. for 3 hours (%) | 0.41 | 0.18 | 0.25 |
| Acid value after heating at 200° C. for 24 hours (mg KOH/g) | 0.665 | 0.480 | 0.711 |
| Hazen number after heating at 200° C. for 24 hours (A.P.H.A. method) | 50 | 60 | 40 |

What we claim is:

1. A process for the production of esters which consists essentially of reacting a mixture of a polycarboxylic acid and an alcohol in the presence or absence of a catalyst which is insoluble in the mixture, distilling off unreacted alcohol from the esterification reaction mixture obtained to give a crude ester, heat-treating said crude ester at a termperature 169-340° C. for 0.1-3 hours, contacting said heat-treated ester with an adsorbent at a temperature of 30-150° C. and then separating and recovering the desired ester from the crude ester.

2. The process of claim 1 wherein the heat-treatment is carried out under reduced pressure to distill off the free polycarboxylic acid resulting from the heat-treatment.

3. The process of claim 1 wherein the heat-treatment is carried out in an atmosphere of an inert gas.

4. The process of claim 1 wherein the adsorption treatment is carried out using an adsorbent selected from the group consisting of sodium oxide, magnesium oxide, aluminum oxide, silicon oxide, iron oxide, calcium oxide, aluminum hydroxide, magnesium hydroxide, sodium carbonate, sodium bicarbonate, aluminum carbonate, magnesium carbonate, and mixtures of these.

5. The process of claim 1 wherein the adsorption treatment is carried out using an absorbent in an amount of not more than 1/20 of the weight of the heat-treated ester.

6. The process of claim 1 wherein the alcohol is an aliphatic or alicyclic monohydric alcohol containing 1 to 13 carbon atoms.

7. The process of claim 1 wherein the polycarboxylic acid is an aromatic polycarboxylic acid, an aliphatic polycarboxylic acid, or an anhydride of any of these polycarboxylic acids.

8. The process of claim 1 wherein the residue left after the separation of the final ester is incinerated.

9. The process of claim 8 wherein the incineration temperature is 400° to 900° C.

10. The process of claim 8 wherein the residual ash obtained by the incineration is re-used as the adsorbent and/or the esterification catalyst.

11. A process for the production of esters which consists essentially of reacting a mixture of a polycarboxylic acid and an alcohol in the presence or absence of a catalyst which is insoluble in the mixture, distilling off unreacted alcohol from the esterification reaction mixture to give a crude ester, heat-treating said crude ester at a temperature of 160°-340° C. for 0.1-3 hours, then contacting said heat-treated ester with an adsorbent at a temperature of 30°-150° C., then separating and recovering the intended ester from the crude ester, thereby forming a residue, incinerating the residue to form ash, and reusing the ash thus obtained as adsorbent and/or esterification catalyst.

* * * * *